United States Patent [19]

Jo et al.

[11] Patent Number: 5,541,086
[45] Date of Patent: Jul. 30, 1996

[54] METHOD FOR THE PRODUCTION OF PORCINE GROWTH HORMONE USING A SYNTHETIC GENE IN YEAST CELLS

[75] Inventors: Jung M. Jo, Seoul; Tae H. Lee, Daejeon; Hyeon H. Jeong, Seoul; Yong B. Lee, Daejeon; Tae G. Lee, Seoul; Yeong W. Park, Daejeon; Kyu B. Han, Daejeon, all of Rep. of Korea

[73] Assignee: Lucky, Ltd., Seoul, Rep. of Korea

[21] Appl. No.: 613,938

[22] Filed: Nov. 13, 1990

Related U.S. Application Data

[63] Continuation of Ser. No. 238,348, filed as PCT/KR87/00015 Dec. 28, 1987 published as WO88/05080 Jul 14, 1988, abandoned.

[30] Foreign Application Priority Data

Dec. 31, 1986 [KR] Rep. of Korea ............ 86-11710

[51] Int. Cl.$^6$ ............ C12P 21/06; C12N 15/18; C07H 17/00; C07K 14/61
[52] U.S. Cl. ............ 435/69.4; 435/69.8; 435/40.1; 435/320.1; 536/23.51; 530/399
[58] Field of Search ............ 435/69.1, 69.4, 435/69.8, 69.9; 530/399, 824, 839, 854; 935/13, 28, 37

[56] References Cited

U.S. PATENT DOCUMENTS

| | | | |
|---|---|---|---|
| 4,443,539 | 4/1984 | Fraser et al. | 435/68 |
| 4,788,144 | 11/1988 | McMullen | 435/70 |

FOREIGN PATENT DOCUMENTS

| | | |
|---|---|---|
| 0104920 | 4/1984 | European Pat. Off. |
| 0111389 | 6/1984 | European Pat. Off. |
| 0208489 | 1/1987 | European Pat. Off. |

OTHER PUBLICATIONS

Glover, 1985 DNA Cloning vol. II IRL Press, Oxford. p. 54.
Seeburg et al 1983 Efficient Bacterial Expression of Bovine and Porcine Growth Hormone DNA 2(1):37.
Holland & Holland 1980 Structural Comparison of Two Nontandomly Repeated Yeast GAP Genes J. Biochem 255(6):2596.
Bennetzen & Hall 1982 Codon Selection in Yeast J. Biol Chem 257:3026.
Bitter & Egan 1984 Expr. of Heterologcus genes in S. Cerevisae from vectors Util. The GAP gene promoter Gene 32:263.
Bennetzen et al *Codon Selection In Yeast*, J. B. C. 257 (6) 3026–31 1982.
Seeburg et al European Patent Application No. 0111 389 D. O. F. Apr. 11, 1983 (furnished by applicant).

*Primary Examiner*—Robert A. Wax
*Assistant Examiner*—K. Cochrane Carlson
*Attorney, Agent, or Firm*—Birch, Stewart, Kolasch & Birch

[57] ABSTRACT

High protein content feed or synthetic steroides are used to elevate the efficiency of feed and promote pig growth. However, the steroids are not metabolized quickly but remain in the body for a long time and may have a detrimental influence on humans. The invention relates to a method for the production of porcine growth hormone which improves the growth of pigs and the efficiency of feed using a synthetic gene in yeast cells. It has been found that porcine growth hormone may be produced economically and in bulk in yeast by gene manipulation technology.

10 Claims, 6 Drawing Sheets

FIG. 1

PGH(5' - 3') : GENE SEQUENCE

```
 U1 : CATGGCGTTCCCGGCTATGCCGCTGAGCTCTCTGTTCGCTAAC  (43mer)
 U2 : GCTGTTTTGCGTGCTCAGCACCTGCACCAACTGGCTGCGGACA  (43mer)
 U3 : CCTACAAAGAATTTGAACGTGCGTACATCCCGGAAGGTCAGCG  (43mer)
 U4 : TTACTCCATCCAGAACGCTCAGGCTGCTTTCTGCTTCTCTGAA  (43mer)
 U5 : ACCATCCCGGCGCCGACCGGTAAAGACGAAGCGCAGCAGCGTT  (43mer)
 U6 : CTGACGTTGAACTGCTGCGTTTCTCTCTGCTGTTGATCCAGTC  (43mer)
 U7 : TTGGCTGGGTCCGGTTCAGTTCCTGTCTAGAGTTTTCACCAAC  (43mer)
 U8 : AGCCTGGTTTTTGGCACCTCTGACCGTGTTTACGAAAAATTGA  (43mer)
 U9 : AAGACCTGGAAGAAGGCATCCAGGCTCTGATGCGTGAACTGGA  (43mer)
U10 : AGATGGTTCTCCGCGTGCAGGTCAGATCCTGAAACAGACCTAT  (43mer)
U11 : GATAAATTTGATACCAACCTGCGTTCTGATGATGCTTTGCTGA  (43mer)
U12 : AAAACTACGGTCTGCTGTCTTGTTTCAAAAAGATCTGCACAA  (43mer)
U13 : AGCTGAAACCTACCTGCGTGTTATGAAATGTCGTCGTTTTGTT  (43mer)
U14 : GAATCTTCTTGTGCTTTCTAG  (21mer)
 L1 : CAGCGGCATAGCCGGGAACGC  (21mer)
 L2 : GCAGGTGCTGAGCACGCAAAACAGCGTTAGCGAACAGAGAGCT  (43mer)
 L3 : TACGCACGTTCAAATTCTTTGTAGGTGTCCGCAGCCAGTTGGT  (43mer)
 L4 : AGCCTGAGCGTTCTGGATGGAGTAACGCTGACCTTCCGGGATG  (43mer)
 L5 : CTTTACCGGTCGGCGCCGGGATGGTTTCAGAGAAGCAGAAAGC  (43mer)
 L6 : GAGAAACGCAGCAGTTCAACGTCAGAACGCTGCTGCGCTTCGT  (43mer)
 L7 : CAGGAACTGAACCGGACCCAGCCAAGACTGGATCAACAGCAGA  (43mer)
 L8 : GGTCAGAGGTGCCAAAAACCAGGCTGTTGGTGAAAACTCTAGA  (43mer)
 L9 : GCCTGGATGCCTTCTTCCAGGTCTTTCAATTTTTCGTAAACAC  (43mer)
L10 : CTGACCTGCACGCGGAGAACCATCTTCCAGTTCACGCATCAGA  (43mer)
L11 : AACGCAGGTTGGTATCAAATTTATCATAGGTCTGTTTCAGGAT  (43mer)
L12 : AAACAAGACAGCAGACCGTAGTTTTTCAGCAAAGCATCATCAG  (43mer)
L13 : CATAACACGCAGGTAGGTTTCAGCTTTGTGCAGATCTTTTTTG  (43mer)
L14 : TCGACTAGAAAGCACAAGAAGATTCAACAAAACGACGACATTT  (43mer)
```

FIG. 2

PGH: LIGATION STRATEGY

| U1 | U2 | U3 | U4 | U5 | U6 | U7 | U8 | U9 | U10 | U11 | U12 | U13 | U14 |
|----|----|----|----|----|----|----|----|----|-----|-----|-----|-----|-----|
| L1 | L2 | L3 | L4 | L5 | L6 | L7 | L8 | L9 | L10 | L11 | L12 | L13 | L14 |

SacI            XbaI            SalI

FIG. 4

```
                                              30
          GCG TTC CCG GCT ATG CCG CTG AGC TCT CTG TTC GCT AAC GCT
          Ala Phe Pro Ala Met Pro Leu Ser Ser Leu Phe Ala Asn Ala
                          60
GTT TTG CGT GCT CAG CAC CTG CAC CAA CTG GCT GCG GAC ACC TAC
Val Leu Arg Ala Gln His Leu His Gln Leu Ala Ala Asp Thr Tyr
    90                                      120
AAA GAA TTT GAA CGT GCG TAC ATC CCG GAA GGT CAG CGT TAC TCC
Lys Glu Phe Glu Arg Ala Tyr Ile Pro Glu Gly Gln Arg Tyr Ser
                      150
ATC CAG AAC GCT CAG GCT GCT TTC TGC TTC TCT GAA ACC ATC CCG
Ile Gln Asn Ala Gln Ala Ala Phe Cys Phe Ser Glu Thr Ile Pro
    180                                     210
GCG CCG ACC GGT AAA GAC GAA GCG CAG CAG CGT TCT GAC GTT GAA
Ala Pro Thr Gly Lys Asp Glu Ala Gln Gln Arg Ser Asp Val Glu
                      240
CTG CTG CGT TTC TCT CTG CTG TTG ATC CAG TCT TGG CTG GGT CCG
Leu Leu Arg Phe Ser Leu Leu Leu Ile Gln Ser Trp Leu Gly Pro
    270                                     300
GTT CAG TTC CTG TCT AGA GTT TTC ACC AAC AGC CTG GTT TTT GGC
Val Gln Phe Leu Ser Arg Val Phe Thr Asn Ser Leu Val Phe Gly
                  330
ACC TCT GAC CGT GTT TAC GAA AAA TTG AAA GAC CTG GAA GAA GGC
Thr Ser Asp Arg Val Tyr Glu Lys Leu Lys Asp Leu Glu Glu Gly
    360                                     390
ATC CAG GCT CTG ATG CGT GAA CTG GAA GAT GGT TCT CCG CGT GCA
Ile Gln Ala Leu Met Arg Glu Leu Glu Asp Gly Ser Pro Arg Ala
                  420
GGT CAG ATC CTG AAA CAG ACC TAT GAT AAA TTT GAT ACC AAC CTG
Gly Gln Ile Leu Lys Gln Thr Tyr Asp Lys Phe Asp Thr Asn Leu
    450                                     480
CGT TCT GAT GAT GCT TTG CTG AAA AAC TAC GGT CTG CTG TCT TGT
Arg Ser Asp Asp Ala Leu Leu Lys Asn Tyr Gly Leu Leu Ser Cys
                      510
TTC AAA AAA GAT CTG CAC AAA GCT GAA ACC TAC CTG CGT GTT ATG
Phe Lys Lys Asp Leu His Lys Ala Glu Thr Tyr Leu Arg Val Met
    540                                     570
AAA TGT CGT CGT TTT GTT GAA TCT TCT TGT GCT TTC TAG
Lys Cys Arg Arg Phe Val Glu Ser Ser Cys Ala Phe End
```

METHOD FOR THE PRODUCTION OF PORCINE GROWTH HORMONE USING A SYNTHETIC GENE IN YEAST CELLS

This application is a continuation of Ser. No. 07/238,348, filed as PCT/KR87/00015 Dec. 28, 1987 published as WO88/05080 Jul. 14, 1988, now abandoned.

BACKGROUND OF THE INVENTION

The present invention relates to a method for the production of porcine growth hormone by a synthetic gene in yeast cells to improve the growth rate of pigs and the efficiency of feed.

Traditionally, pig breeders have used feed with a high protein content or synthetic steroids in order to promote growth and elevate the efficiency of feed. But because feed with steroid supplements is not metabolized quickly but remains in the body for a long time and has a detrimental influence on humans, developed nations are prohibiting its use.

Taking this into account, the present inventors have discovered that porcine growth hormone maybe produced economically and in bulk in yeast by gene manipulation technology and intend to apply this discovery to the pig breeding business.

Therefore, they have accomplished this by discovering that as a result of using yeast cells, in a manner different from other processes previously known (Seeburg et al. DNA2(1983), 37), natural and mature porcine growth hormone in which the N-terminus is initiated from ala maybe mass-produced.

SUMMARY OF THE INVENTION

The object of the present invention is to provide a method for the production of porcine growth hormone by using yeast as a host for expression vector.

Namely, the method for the production of porcine growth hormone by using yeast as a host for expression vector comprises; (a) synthesizing oligonucleotides with SacI, XbaI and SalI restriction sites based on amino acid sequence of porcine growth hormone, (b) cloning the C-terminal XbaI/SalI fragment of the synthetic oligonucleotides ligated by the ligation strategy to an E.coli vector, pUC18, which is treated with XbaI/SalI restriction enzymes, (c) cloning the N-terminal SacI/XbaI fragment of synthetic oligonucleotides treated with SacI/XbaI restriction enzyme to the above cloned vector to produce the porcine growth hormone lacking a portion of the N-terminus, (d) cloning the porcine growth hormone gene and N-terminal synthetic adaptor to an E.coli vector comprising a promoter and a terminator to produce a cassette of a promoter-porcine growth hormone gene with an N-terminal synthetic adaptor-terminator, (e) recloning the cassette to a yeast expression vector and (f) expressing the resultant vector in yeast cells.

The N-terminal synthetic adaptor gene has the following base sequence with NcoI and SacI restriction sites;

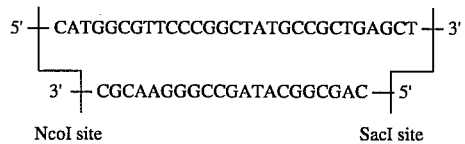

NcoI site              SacI site

The resulting expression vector is the vector (pC1/1-PGH) cloned of a cassette comprising the promoter-porcine growth hormone gene with an N-terminal synthetic adaptor-terminator, a complete 2 micron gene, a Leu 2d gene and an origin of replication.

BRIEF DESCRIPTION OF THE DRAWINGS

FIG. 1 shows synthetic oligonucleotides corresponding to the porcine growth hormone gene and represented by the base sequence from the 5'-end to the 3'-end.

FIG. 2 is a ligation strategy of oligonucleotides.

FIG. 4 is the base sequence and putative amino acid sequence of confirmed porcine growth hormone gene.

DETAILED DESCRIPTION OF A PREFERRED EMBODIMENT

The present inventors have selected the base sequence of porcine growth hormone gene with an amino acid codon preferentially used in yeast cells, based upon the amino acid sequence of porcine growth hormone reportedly Seeburg et al. [DNA 2(1983) 37], and the total gene of mature porcine growth hormone in the natural state, in which the N-terminus initiates with ala, is chemically synthesized with a gene synthesizer (Applied Biosystem Model 380B, U.S.A.) according to the phosphoramidate's method.

The synthetic oligonucleotides are ligated as shown in FIG. 2 and cloned to an E. coli vector, pUC18, [Norrander et al. Gene 36 (1983) 101–106] to preduce a vector pPGH(552) comprising a SacI/SalI restriction fragment of 552 base pairs, which does not have an N-terminal region of a mature porcine growth hormone gene of 579 base pairs (Refer to FIG. 3).

Figure 5:
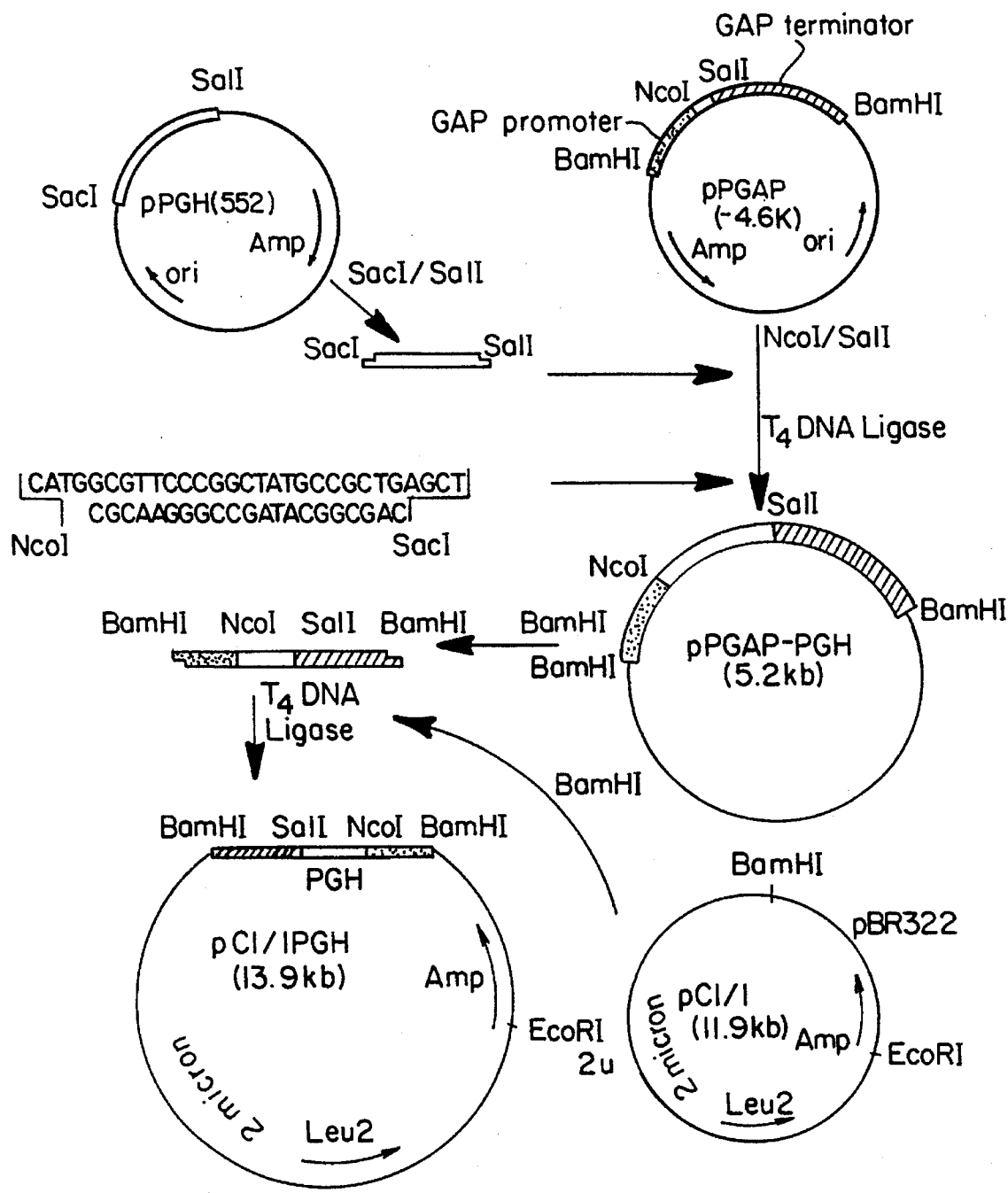
FIG. 5 is a cloning process for a vector of E.coli (pPGAP) and a yeast expression vector (pC1/1) to produce porcine growth hormone in yeast.

In order to produce a clone comprising the complete porcine growth hormone gene and express it in a yeast host, the SacI/SalI fragment was separated from pPGH(552) and a synthetic adaptor was inserted between the NcoI site and the SalI site of the vector comprising a promoter and a terminator gene, pPGAP [Clontech Lab, Palo Alto, Calif. 94303, U.S.A. Holland, J. P. & Holland, J. J. J. of Biological Chemistry 255, 2596–2605 (1980), Bitter, G. A. & Egan, K. M. Gene 32, 263–274 (1984); 20B-12, Zhu, X. L. et al., Mol. Gen. Genet 9194, 31–41(1984); ATCC 34025] to obtain pPGAP-PGH (579), wherein the adaptor chemically synthesized is comprised of an NcoI restriction site, an initiation codon and some amino acid codons corresponding to the N-terminal region (Refer to Example 3).

pPGAP-PGH(579) is treated with BamHI restriction enzyme to separate the BamHI fragment (abut 1970 base pairs) comprising a promoter, the porcine growth hormone gene and a terminator. The BamHI fragment is inserted into the BamHI restriction site of a yeast expression vector, pC1/1, which is autonomously replicated in E.coli and yeast [ATCC 37115; Brake et al., Proc. Natl. Acad. Sci U.S.A. 81 (1984), 4642], to produce pC1/1-PGH (Refer to FIG. 5).

The expression vector is cloned to a yeast strain DCO4 [Yeast Genetic Stock Center, Broach, J. R. & Hicks, J. B. Cell 21, 501 (1980)] by means of the method of Hinnen et al. The transformed yeast cell was cultured in YEPD medium comprising 2% glucose as in Example 5 for 24 hrs, porcine growth hormone was produced depending on growth rate of the cell and 200 mg of porcine growth hormone per liter of culture can be obtained at the $OD_{650}=20$.

The invention is illustrated by the following Examples, without them limiting its range.

Example 1 : Ligation of Synthetic Oligonucleotides of Porcine Growth Hormone Gene and Cloning to Vector pUC18

In order to obtain the complete porcine growth hormone gene from the synthetic oligonucleotides having the gene sequences of FIG. 1, ligation strategy such as in FIG. 2 and vector pUC18 comprising SacI, SalI, XbaI, etc. restriction sites were used.

The oligonucleotides (U7–U14/L8–L14) corresponding to the 3'-end of the XbaI and SalI restriction fragments from synthetic oligonucleotides were collected at the amount that the $OD_{260}$ of each oligonucleotide equals to 0.05 and then separately dried. Four units of T4 polynucleotide kinase were added to a total volume of 30 µl in the presence of a buffer solution comprising 50 mM Tris-HCl(pH7.5), 1 mM ATP, 1 mM DTT and 10 mM $MgCl_2$ and they were reacted at 37° C. for 30 mins. to phosphorylate the 5'-end residue of the oligonucleotides. After the oligonucleotides were pooled and treated with an equal volume of phenol and chloroform mixture, they were precipitated with ethanol. The precipitate was dissolved in 53 µl of a buffer solution comprising 60 mM Tris-HCl (pH7.5), 1 mM DTT and 10 mM $MgCl_2$. The solution was placed in a 95° C. water bath and kept at room temperature for 6 hrs. so that as its temperature drops slowly, each oligonucleotide produced base pairing with complementary sequence.

T4 DNA ligase (20 units) and 5 µl of 10 mM ATP were added and the 5'- and 3'-ends of the oligonucleotides were ligated at room temperature for 10 mins. The above solution was treated with phenol and chloroform mixture and precipitated with ethanol.

Ten units each of XbaI and SalI restriction enzymes were added to the precipitated nucleic acid in the presence of a buffer solution comprising 60 mM Tris(pH7.6), 10 mM $MgCl_2$ and 100 mM NaCl and reacted at 37° C. for 1 hr.

After 7% polyacrylamide gel electrophoresis of the above mixture, a band corresponding to 200–300 base pairs was cut from the gel. After electroelution, the precipitates were dissolved in 20 µl of distilled water.

Three µl of DNA and 10 ng of a vector, pUC18, cut with XbaI and SalI restriction enzymes were ligated in the presence of the ligation solution comprising 60 mM Tris-HCl(pH7.5), 10 mM DTT, 10 mM $MgCl_2$, 1 mM ATP and 10 units of T4 DNA ligase at 14° C. for 16 hrs.

*E.coli* JM103[BRL, U.S.A., Messing, J., *Methods in Enzymology*, 103, 20–78 (1983)] competent cells were added to the ligation reactant and transformed according to Hanshan's method [J.Mel. Biol 116, 557(1983)] at 37° C.

The clone containing p3'-PGH was selected from the white colonies by using Birnboim and Doly's method [*Nucleic Acid Res.* 7, 1513 (1979)].

Figure 3:
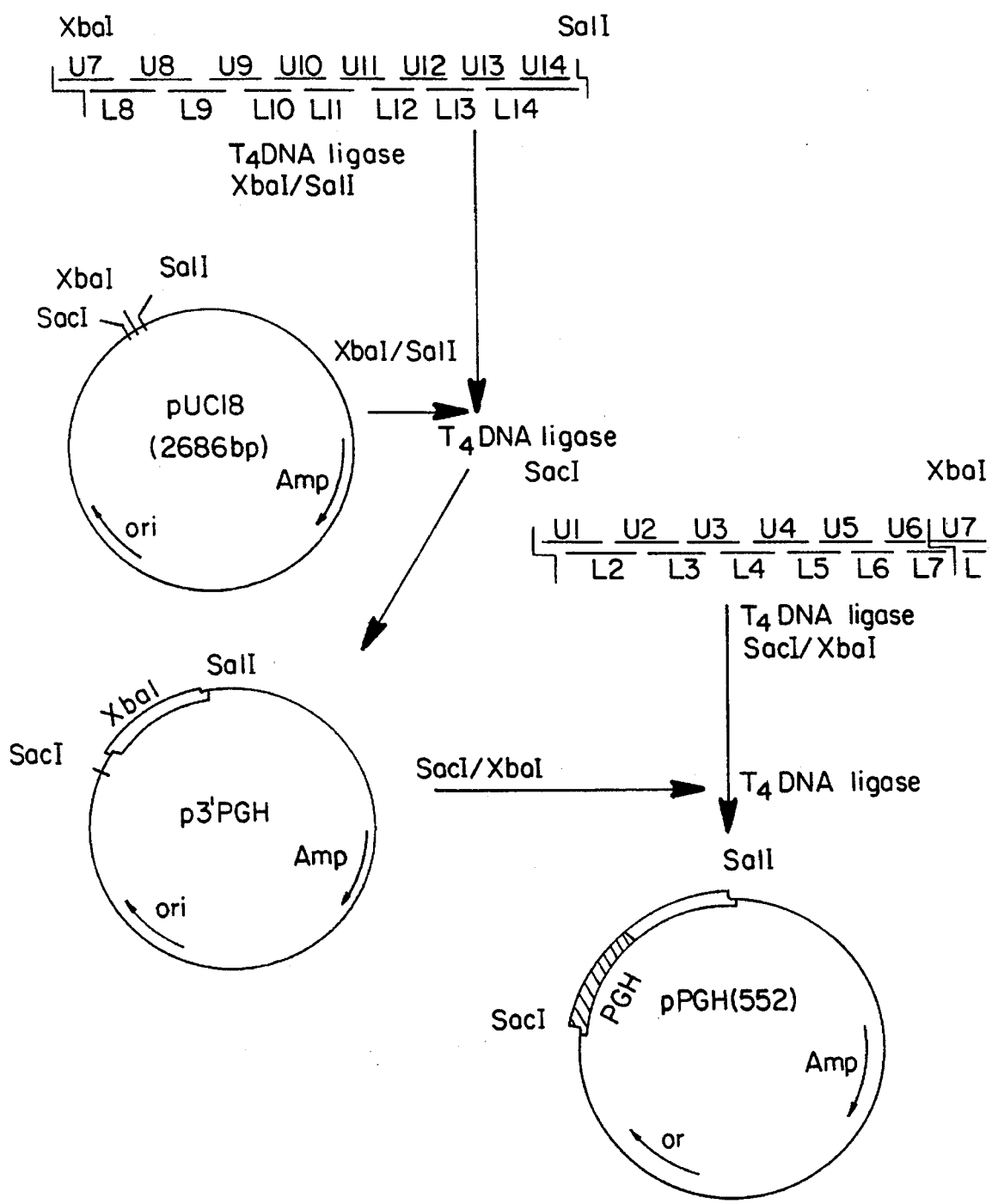
FIG. 3 is a schematic cloning strategy of synthetic oligonucleotides to a vector of E.coli (pUC18).

On the other hand, the oligonucleotides (U1–U7/L2–L8) corresponding to the 5'-end SacI and XbaI restriction fragment of the complete porcine growth hormone gene were ligated by the same method as mentioned above and ligated to the p3'-PCH vector cut with SacI and XbaI restriction enzymes to produce pPGH(552) as shown in FIG. 3. The nucleotide sequence was confirmed by Sanger's dideoxy sequencing method [*Proc. Natl. Acad. Sci. U.S.A.* 74, 5473–5477] (Refer to FIG. 4).

Example 2: Manipulation of Synthetic Porcine Growth Hormone Gene for Expression in Yeast Cell pPGH(552) does not comprise 9 amino acids in the 5'-residue of a complete porcine growth hormone and in order to clone the complete porcine growth hormone gene and to have it expressed in yeast cells, the deficient part of the 5'-end was synthesized by the gene synthesizer. The adaptor comprising the NcoI restriction site, the initiation codon and the codon corresponding to 8 amino acids was synthesized by selecting codons preferentially used in yeast cells and the SacI restriction site was synthesized at the other end (Refer to FIG. 5).

The process of cloning was as follows; pPGH(552) was treated with SacI and SalI restriction enzymes to obtain a restriction fragment corresponding to 552 base pairs and the fragment was separated through agarose gel electrophoresis. The fragment and the synthetic adaptor were inserted between the NcoI and SalI restriction sites of a vector, pPGAP, comprising a promoter and a terminator. The detailed procedures are as follows: The 5'-end of each synthetic adaptor was phosphorylated with T4 polynucleotide kinase as described in Example 1. One µl of each phosphorylation solution, 3 µl (30 ng) of the SacI/SalI fragment separated from pPGH(552) and 1 µl (7 ng) of vector pPGAP cut with NcoI and SalI restriction enzymes were mixed and kept at 65° C. for 15 mins. They were cooled slowly to room temperature. Two µl of 10 mM ATP, 2 µl of a 10-fold concentrated ligation reaction buffer solution, 1 µl of ligase and 8 µl of distilled water were added and reacted at 14° C. for 16 hrs.

Based upon the method as in Example 1, the above was used to transform *E.coli* cell HB101 [ATCC 37017], and pPGAP-PGH comprising the promoter, the complete porcine growth hormone gene and the terminator for expression in yeast was produced.

The vector, pPGAP, contains a glyceraldehyde-3'-phosphate dehydrogenase promoter, a constitutive promoter which is expressed according to the growth of the cell end a terminator. pPGAP-PGH was treated with BamHI restriction enzyme to separate the BamHI restriction fragment about 1,970 base pairs, comprising a glyceraldehyde-3'-phosphate dehydrogenase promoter, a porcine growth hormone gene and a glyceraldehyde-3'-phosphate dehydrogenase terminator. The BamHI restriction fragment was inserted into the BamHI restriction site of the expression vector pC1/1 which can be replicated in yeast cells, to produce pC1/1-PGH (Refer to FIG. 5).

The pC1/1-PGH gene was used to transform yeast strain DCO4 according to Hinnen's method [Proc Natl. Acad. Sci, U.S.A. 75 (1978), 1929].

After culturing at 30° C. for 5 days, a recombinant clone with porcine growth hormone gene was picked and identified by the method such as in Example 3.

Example 3: Cultivation of Yeast for Producing Porcine Growth Hormone and Its Identification Each 3 ml of yeast cells transformed with vector pC1/1-PGH was cultured in a culture medium without leucine (6.7 g of Yeast Nitrogen Base without amino acids, 0.25 g of leu-deficient supplements and 6% glucose per 1 of culture medium) at 30° C. for 24 hrs. The culture was added to 100 ml of YEPD culture medium comprising 2% peptone, 1% yeast extract and 2% glucose and cultured at 30° C. for 24 hrs.

At the $OD_{650}$ equaled to around 40, the fraction corresponding to $OD_{650}$ of 10 was collected and centrifuged. It is dissolved in 400 μl of a buffer solution containing 10 mM Tris-HCl(pH 7.5), 1 mM EDTA, 2 mM phenyl methyl sulfonyl fluoride and 8M urea and glass beads, 0.45 mm in diameter with the same volume, were added and shaken vigorously. After rupturing the cell wall and letting porcine growth hormone elute into the buffer solution, 4 μl of eluted solution was executed by electrophoresis on 12.5% SDS polyacrylamide gel.

Figure 6:
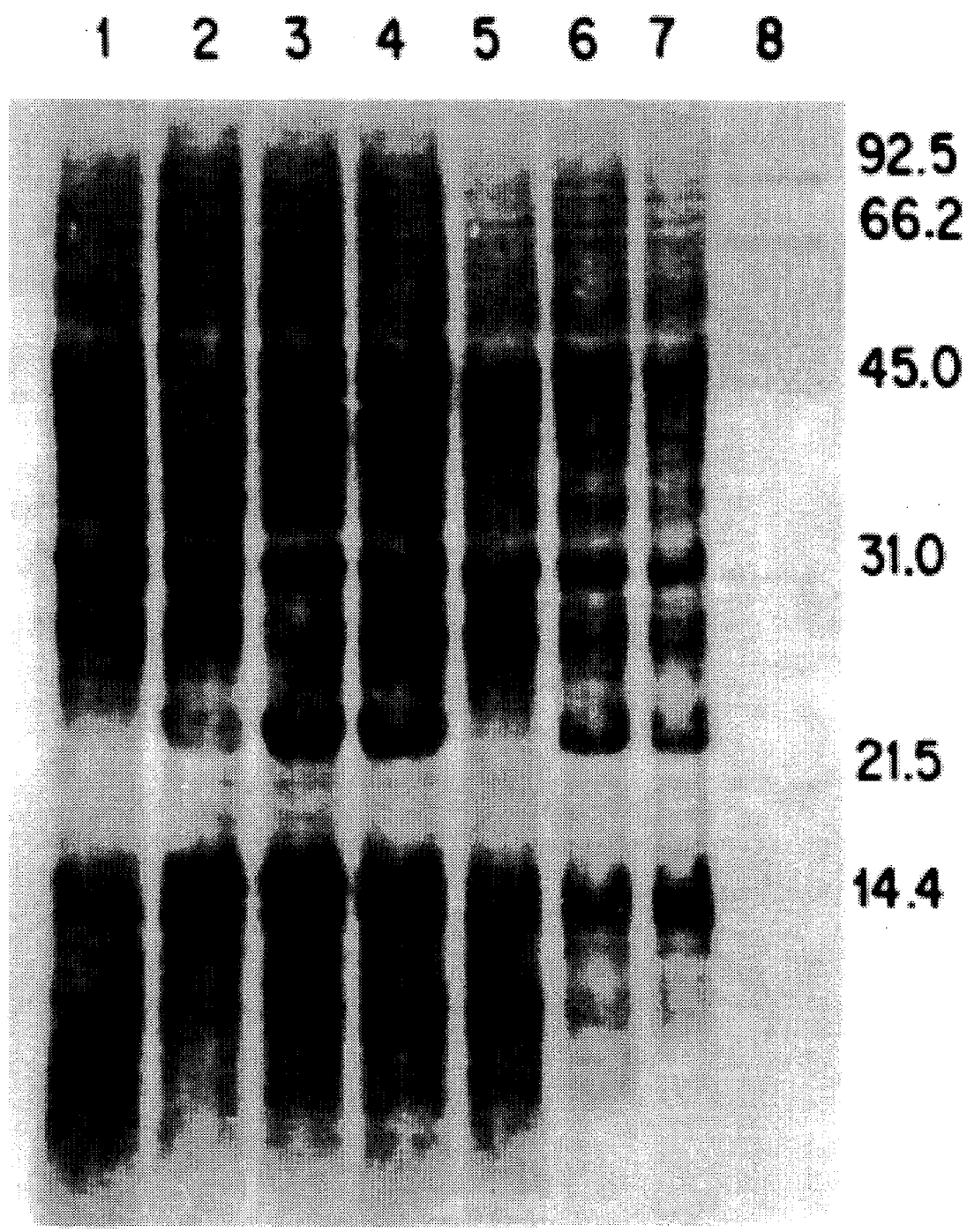
FIG. 6 are the results confirmed by SDS-polyacrylamide gel electrophoresis of porcine growth hormone produced in yeast cells.

The results are represented in FIG. 6; Lane 8 represents the standad M.W. of protein from the BioRad company.

Lanes 1 and 5 represent total proteins of yeast cells transformed with the vector pC1/1 without porcine growth hormone gene.

Lanes 2–4 represent total proteins of yeast cells transformed with the vector pC1/1-PGH containing the porcine growth hormone gene.

As shown in lanes 2–4 of FIG. 6, it is evident by gel scanning that porcine growth hormone appears at a band about 22 Kd in an amount corresponding to 10% of the total protein.

The amino acid sequence confirmed (Biomedical Resource Center, University of Calfornia, San Francisco) shows the mature porcine growth hormone starting from alanine and in which methionine might be processed by amino peptidase in vivo.

We claim:

1. A method for the production of porcine growth hormone in a yeast cell which comprises:

1) transforming said yeast cell with a recombinant DNA plasmid comprising a cassette of a constitutive promoter operatively linked to a porcine growth hormone gene and a terminator sequence operatively linked to a porcine growth hormone gene, said porcine growth hormone gene having the structure

5'-ATGGCGTTCCCGGCTATGCCGCTGAGC-3' as the nucleotide sequence which encodes the initiation codon, the alanine amino-terminal amino acid of the mature porcine growth hormone and the 7 amino acids proximal to the amino-terminus of the mature porcine growth hormone, 2) culturing said transformed yeast cell, and 3) recovering the porcine growth hormone from said culture.

2. The method of claim 1, wherein said constitutive promoter is the promoter from a glyceradehyde-3-phosphate dehydrogenase gene.

3. The method of claim 2, wherein said terminator is the transcription terminator from a glyceraldehyde-3-phosphate dehydrogenase gene.

4. The method of claim 1, wherein said porcine growth hormone gene further comprises the synthetic oligonucleotides shown in FIG. 1.

5. The method of claim 3, wherein said porcine growth hormone gene further comprises the synthetic oligonucleotides shown in FIG. 1.

6. The method of claim 1, wherein said recombinant DNA plasmid is pC1/1PGH, a map of which is drawn in FIG. 5.

7. The method of claim 2, wherein the culturing step (2) is performed in medium comprising water, 6.7 g/liter Yeast Nitrogen Base without amino acids, 0.25 g/liter leucine-deficient supplements and 6% glucose.

8. The method of claim 7, wherein the culturing step (2) further comprises culturing in a medium comprising 2% peptone, 1% yeast extract and 2% glucose.

9. The method of claim 6, wherein the culturing step (2) is performed in medium comprising water, 6.7 g/liter Yeast Nitrogen Base without amino acids, 0.25 g/liter leucine-deficient supplements and 6% glucose.

10. The method of claim 9, wherein the culturing step (2) further comprises culturing in a medium comprising 2% peptone, 1% yeast extract and 2% glucose.

* * * * *